United States Patent
Lim et al.

(10) Patent No.: US 10,556,918 B2
(45) Date of Patent: Feb. 11, 2020

(54) METHOD FOR PREPARING AMINOSILANE-BASED COMPOUND

(71) Applicant: LG Chem, Ltd., Seoul (KR)

(72) Inventors: Won Taeck Lim, Daejeon (KR); Ji Eun Kim, Daejeon (KR); Cheol Jae Kim, Daejeon (KR); Won Mun Choi, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/758,873

(22) PCT Filed: Apr. 20, 2017

(86) PCT No.: PCT/KR2017/004247
§ 371 (c)(1),
(2) Date: Mar. 9, 2018

(87) PCT Pub. No.: WO2017/191914
PCT Pub. Date: Nov. 9, 2017

(65) Prior Publication Data
US 2018/0282353 A1    Oct. 4, 2018

(30) Foreign Application Priority Data

May 3, 2016   (KR) ........................ 10-2016-0054881

(51) Int. Cl.
| | | |
|---|---|---|
| C07F 7/08 | (2006.01) | |
| C07F 7/18 | (2006.01) | |
| C08K 5/544 | (2006.01) | |
| C07F 7/20 | (2006.01) | |

(52) U.S. Cl.
CPC .............. C07F 7/1892 (2013.01); C07F 7/08 (2013.01); C07F 7/1804 (2013.01); C07F 7/20 (2013.01); C08K 5/544 (2013.01); C08K 5/5442 (2013.01)

(58) Field of Classification Search
CPC .................................................. C07F 7/1892
See application file for complete search history.

(56) References Cited

U.S. PATENT DOCUMENTS

| | | |
|---|---|---|
| 3,682,975 A | 8/1972 | Tesoro |
| 6,486,286 B1 | 11/2002 | McGall et al. |
| 2009/0203843 A1 | 8/2009 | Fukuoka et al. |
| 2011/0118496 A1 | 5/2011 | Just et al. |
| 2011/0146877 A1 | 6/2011 | Tanaka et al. |
| 2014/0120244 A1 | 5/2014 | Wang et al. |
| 2016/0177011 A1 | 6/2016 | Kim et al. |

FOREIGN PATENT DOCUMENTS

| | | |
|---|---|---|
| CN | 101597302 A | 12/2009 |
| CN | 102026826 A | 4/2011 |
| CN | 104140437 A | 11/2014 |
| JP | S59144793 A | 8/1984 |
| JP | H0657767 B23 | 8/1994 |
| JP | 2008056850 A | 3/2008 |
| JP | 2010215610 A | 9/2010 |
| JP | 2011121906 A | 6/2011 |
| JP | 2013032563 A | 2/2013 |
| JP | 2014128786 A | 7/2014 |
| JP | 2016017097 A | 2/2016 |
| KR | 20150044799 A | 4/2015 |
| KR | 20150141390 A | 12/2015 |
| KR | 20160032708 A | 3/2016 |
| WO | 0021967 A1 | 4/2000 |
| WO | 2005099689 A1 | 10/2005 |
| WO | 2008013090 A1 | 1/2008 |

OTHER PUBLICATIONS

Search Report for Chinese Application No. 2017800032945, dated Dec. 13, 2019 (2 pages).

*Primary Examiner* — Paul V Ward
(74) *Attorney, Agent, or Firm* — Lerner, David, Littenberg, Krumholz & Mentlik, LLP

(57) ABSTRACT

The present invention provides a novel method for preparing an aminosilane-based compound, by which an aminosilane-based compound used for preparing a modified and conjugated diene-based polymer which shows excellent affinity with an inorganic filler in a rubber composition and increases dispersibility, may be prepared in high purity and high yield.

16 Claims, No Drawings

METHOD FOR PREPARING AMINOSILANE-BASED COMPOUND

CROSS-REFERENCE TO RELATED APPLICATIONS

The present application is a national phase entry under 35 U.S.C. § 371 of International Application No. PCT/KR2017/004247 filed Apr. 20, 2017, which claims priority from Korean Patent Application No. 10-2016-0054881, filed on May 3, 2016, the entire contents of which are incorporated herein by reference.

TECHNICAL FIELD

The present invention relates to a novel method for preparing an aminosilane-based compound with high purity in high yield.

BACKGROUND ART

Recently, as interest in energy conservation and environmental issues is rising, the decrease of a fuel consumption ratio of cars is required. As one method for realizing the requirement, a method for decreasing exothermic properties in tires using an inorganic filler such as silica and carbon black in a rubber composition for forming tires has been suggested. However, the dispersion of the inorganic filler in the rubber composition is not easy, and the physical properties of the rubber composition such as abrasion resistance, cracking resistance and processability are rather degraded.

To solve such limitations and to increase the dispersibility of an inorganic filler such as silica and carbon black in a rubber composition, a method for modifying a polymerization active part of a conjugated diene-based polymer obtained by anionoic polymerization using an organic lithium, using a functional group which may interact with an inorganic filler has been developed. Particularly, a method of modifying a polymerization active terminal of a conjugated diene-based polymer into a tin-based compound or introducing an amino group into thereof, a method of modifying thereof into an alkoxysilane derivative, or the like has been suggested. However, when preparing a rubber composition using the modified and conjugated diene-based polymer which is modified by the above-described method, low exothermic properties may be secured, but the improving effects of physical properties of the rubber composition such as abrasion resistance, processability, or the like are insufficient.

DISCLOSURE OF THE INVENTION

Technical Problem

A first technical task for solving in the present invention is to provide a novel method for preparing an aminosilane-based compound introducing an amino group, in high purity and high yield.

In addition, a second technical task for solving in the present invention is to provide a novel compound useful for the preparation of the aminosilane-based compound.

However, the technical tasks for accomplishing in the present invention are not limited to the above-mentioned tasks, but unmentioned other tasks also may be distinctly understood by a person skilled in the art from the details below.

Technical Solution

To solve the above-described tasks, there is provided according to an embodiment of the present invention, a method for preparing an aminosilane-based compound of the following Formula 1, including a step of reacting a compound of the following Formula 2 with a hetero compound containing at least one nitrogen atom:

[Formula 1]

[Formula 2]

in Formula 1 and Formula 2,

A is a functional group derived from the hetero compound containing at least one nitrogen atom, $X^1$ is a halogen group, Y is a divalent hydrocarbon group of 1 to 20 carbon atoms, and $Z^1$ and $Z^2$ are each independently a functional group of the following Formula 3:

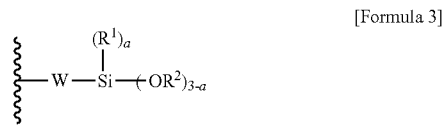

[Formula 3]

in Formula 3,

"a" is an integer of 0 to 2, $R^1$ and $R^2$ are each independently a monovalent hydrocarbon group of 1 to 10 carbon atoms, and W is a divalent hydrocarbon group of 1 to 10 carbon atoms, which is unsubstituted or substituted with an alkyl group of 1 to 4 carbon atoms.

In addition, according to another embodiment of the present invention, there is provided a method for preparing an aminosilane-based compound of the following Formula 1, including a step of reacting a compound of the following Formula 2 with a hetero compound containing at least one nitrogen atom:

[Formula 1]

[Formula 2]

in Formula 1 and Formula 2,

A is a functional group derived from the hetero compound containing at least one nitrogen atom, $X^1$ is a halogen group, Y is a divalent hydrocarbon group of 1 to 20 carbon atoms, and $Z^1$ and $Z^2$ are each independently a monovalent hydrocarbon group of 1 to 20 carbon atoms, which is unsubstituted or substituted with an organic group containing Si, O or N and does not contain active hydrogen, or a functional group of the following Formula 3, wherein at least one of the two is the functional group of the following Formula 3:

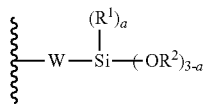

[Formula 3]

in Formula 3, "a", $R^1$, $R^2$ and W are the same as defined above.

According to another embodiment of the present invention, there is provided a compound of the following Formula 2, which is useful for the preparation of the aminosilane-based compound of Formula 1:

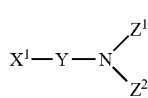

[Formula 2]

in Formula 2,

A is a functional group derived from a hetero compound containing at least one nitrogen atom, $X^1$ is a halogen group, Y is a divalent hydrocarbon group of 1 to 20 carbon atoms, and $Z^1$ and $Z^2$ are each independently a monovalent hydrocarbon group of 1 to 20 carbon atoms, which is unsubstituted or substituted with an organic group containing Si, O or N and does not contain active hydrogen, or a functional group of the following Formula 3, wherein at least one of the two is the functional group of the following Formula 3:

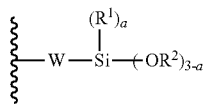

[Formula 3]

in Formula 3, "a", $R^1$, $R^2$ and W are the same as defined above.

Other details of exemplary embodiments of the present invention are included in detailed description below.

Advantageous Effects

According to the method for preparing an aminosilane-based compound according to the present invention, by selectively and sequentially introducing an alkoxysilylamino group and a functional group derived from a hetero compound, particularly, an amino group using a halogenated alkane compound containing halogen functional groups having different reactivity in a molecule, an aminosilane-based compound with high purity may be prepared in high yield, and there is no concern on the remaining of unreacted secondary aminosilane and the removal thereof.

In addition, since the aminosilane-based compound prepared by the preparation method has excellent interaction with a modified and conjugated diene-based polymer, a modified and conjugated diene-based polymer may be prepared with excellent efficiency.

Also, the modified and conjugated diene-based polymer thus prepared has high compatibility with an inorganic filler, and if applied in a rubber composition, exothermic properties, tensile strength, abrasion resistance, a low consumption ratio and wet traction may be improved.

BEST MODE FOR CARRYING OUT THE INVENTION

Hereinafter, the present invention will be described in more detail in order to assist the understanding of the present invention.

It will be understood that words or terms used in the specification and claims shall not be interpreted as the meaning defined in commonly used dictionaries. It will be further understood that the words or terms should be interpreted as having a meaning that is consistent with their meaning of the technical idea of the invention, based on the principle that an inventor may properly define the meaning of the words or terms to best explain the invention.

The terms "monovalent hydrocarbon group" used in the present invention refers to a monovalent substituent derived from a hydrocarbon group, and for example, may refer to a monovalent atomic group in which carbon of an alkyl group, an alkenyl group, an alkynyl group, a cycloalkyl group, a cycloalkyl group containing at least one unsaturated bond and an aryl group is combined with hydrogen. The monovalent atomic group may have a linear or branched structure according to the structure of the combination.

The terms "divalent hydrocarbon group" used in the present invention refers to a divalent substituent derived from a hydrocarbon group, and for example, may refer to a divalent atomic group in which carbon of an alkylene group, an alkenylene group, an alkynylene group, a cycloalkylene group, a cycloalkylene group containing at least one unsaturated bond and an arylene group is combined with hydrogen. The divalent atomic group may have a linear or branched structure according to the structure of the combination.

A functional group containing a heteroatom, particularly, an aminosilane-based modifier including a heterocyclic group has excellent interaction with a rubber polymer, and a modified and conjugated diene-based polymer prepared using thereof has high compatibility with an inorganic filler in a rubber composition, thereby improving physical properties of a rubber composition such as exothermic properties. Such aminosilane-based modifier including a heterocyclic group is generally prepared by the reaction of a heterocycle-containing alkylhalogen derivative and an aminosilane derivative, but has limitations of low preparation yield, and difficulty in separating and removing an unreacted secondary aminosilane derivative.

Accordingly, the present invention provides a method for preparing an aminosilane-based compound, by which an aminosilane-based compound with high purity may be prepared in high yield without concerning the remaining of unreacted secondary aminosilane and the removal thereof during preparing an aminosilane-based compound, by selectively and sequentially introducing an alkoxysilylamino group and a functional group derived from a hetero compound containing at least one nitrogen atom, by using a halogenated alkane compound containing halogen functional groups having different reactivity in a molecule.

Particularly, the preparation method of an aminosilane-based compound according to an embodiment of the present invention includes a step of reacting a compound of the following Formula 2 with a hetero compound containing at least one nitrogen atom:

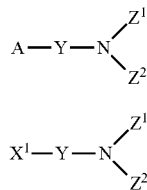

[Formula 1]

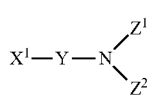

[Formula 2]

in Formula 1 and Formula 2,

A is a functional group derived from the hetero compound containing at least one nitrogen atom, $X^1$ is a halogen group, Y is a divalent hydrocarbon group of 1 to 20 carbon atoms, more particularly, 2 to 20 carbon atoms, and $Z^1$ and $Z^2$ are each independently a monovalent hydrocarbon group of 1 to 20 carbon atoms, which is unsubstituted or substituted with an organic group containing Si, O or N and does not contain active hydrogen, or a functional group of the following Formula 3, in which at least one of the two is the functional group of the following Formula 3, and more particularly, $Z^1$ and $Z^2$ are each independently a functional group of the following Formula 3:

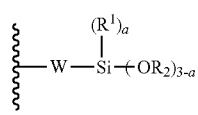

[Formula 3]

in Formula 3,

"a" is an integer of 0 to 2, $R^1$ and $R^2$ are each independently a monovalent hydrocarbon group of 1 to 10 carbon atoms, and W is a divalent hydrocarbon group of 1 to 10 carbon atoms, which is unsubstituted or substituted with an alkyl group of 1 to 4 carbon atoms, particularly, an alkylene group of 1 to 10 carbon atoms, which is unsubstituted or substituted with an alkyl group of 1 to 4 carbon atoms.

In addition, in the preparation method, the compound of Formula 2 may be prepared by reacting a compound of Formula 4 below and a compound of Formula 5 below in the presence of a base. Accordingly, the method for preparing an aminosilane-based compound according to an embodiment of the present invention may further include a step of preparing the compound of Formula 2 by reacting a compound of Formula 4 below and a compound of Formula 5 below in the presence of a base, prior to the reaction of the compound of Formula 2 and the hetero compound containing at least one nitrogen atom.

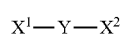

[Formula 4]

[Formula 5]

in Formula 4 and Formula 5, $X^1$ and $X^2$ are each independently a halogen group, where $X^2$ is a halogen group having a smaller electronegativity than $X^1$, Y is a divalent hydrocarbon group of 1 to 20 carbon atoms, more particularly, 2 to 20 carbon atoms, and $Z^1$ and $Z^2$ are each independently a monovalent hydrocarbon group of 1 to 20 carbon atoms, which is unsubstituted or substituted with an organic group containing Si, O or N and does not contain active hydrogen, or the functional group of Formula 3, in which at least one of the two is the functional group of Formula 3, and more particularly, $Z^1$ and $Z^2$ are each independently the functional group of Formula 3.

Meanwhile, in the present invention, the active hydrogen is hydrogen in an atomic state with high reactivity, and means a hydrogen atom bonded to O, N, or the like, which has high electronegativity in OH, $NH_2$, or the like.

More particularly, the method for preparing an aminosilane-based compound according to an embodiment of the present invention includes a step of preparing the compound of Formula 2 by reacting the compound of Formula 4 and the compound of Formula 5 in the presence of a base (step 1); and a step of preparing the aminosilane-based compound of Formula 1 by reacting the compound of Formula 2 with a hetero compound containing at least one nitrogen atom (step 2).

Step 1 of the preparation method of the aminosilane-based compound of Formula 1 according to an embodiment of the present invention is a step of preparing the compound of Formula 2 by reacting the compound of Formula 4 and the compound of Formula 5 in the presence of a base.

The compound of Formula 4 includes two halogen groups having different reactivity in a molecule, to allow the sequential and selective introduction of an alkoxysilylamino group and a hetero group.

The smaller the electronegativity of a halogen group is, the easier a substitution reaction occurs. Particularly, the reactivity in a substitution reaction is in the order of F<Cl<Br<I. In an embodiment, if $X^2$ is a bromo group and $X^1$ is a chloro group or a fluoro group, the reaction is selectively performed at a halogen group having smaller electronegativity and higher reactivity among $X^1$ and $X^2$, that is, $X^2$ during the reaction with Formula 5. In addition, a halogen group not participated in the reaction, that is, $X^1$ may participate in a subsequent step, for example, a reaction with a hetero compound.

Particularly, the compound of Formula 4 may be a compound of Formula 4 where $X^1$ and $X^2$ are each independently a halogen group such as a fluoro group, a chloro group, a bromo group, and an iodine group, and $X^2$ may be a halogen group having smaller electronegativity and greater reactivity than $X^1$.

In addition, the compound of Formula 4 may be a compound of Formula 4 where Y is a divalent hydrocarbon group of 1 to 20 carbon atoms, particularly, 2 to 20 carbon atoms, more particularly, an alkylene group of 2 to 20 carbon atoms, further more particularly, a linear alkylene group of 2 to 8 carbon atoms, and may be a compound with linear alkylene group of 3 to 5 carbon atoms in consideration of the reactivity with a hetero compound and the improving effect of the interaction of a finally prepared aminosilane-based compound of Formula 1 with a conjugated diene-based polymer.

More particularly, the compound of Formula 4 may be 1,2-bromochloroethane, 1,2-chlorofluoroethane, 1,2-chloroiodoethane, 1,2-bromofluoroethane, 1,2-fluoroiodoethane, 1,2-bromoiodoethane, 1,3-bromochloropropane, 1,3-chlorofluoropropane, 1,3-chloroiodopropane, 1,3-bromofluoropropane, 1,3-fluoroiodopropane, 1,3-bromoiodopropane, 1,4-bromochlorobutane, 1,4-chlorofluorobutane, 1,4-chloroiodobutane, 1,4-bromofluorobutane, 1,4-fluoroiodobutane, 1,4-bromoiodobutane, 1,5-bromochloropentane, 1,5-chlorofluoropentane, 1,5-chloroiodopentane, 1,5-bromofluoropentane, 1,5-fluoroiodopentane, 1,5-bromoiodopentane, 1,6-bromochlorohexane, 1,6-chlorofluorohexane, 1,6-chloroiodohexane, 1,6-bromofluorohexane, 1,6-fluoroiodohexane, 1,6-bromoiodohexane, 1,7-bromochloroheptane, 1,7-chlorofluoroheptane, 1,7-chloroiodoheptane, 1,7-bromofluoroheptane, 1,7-fluoroiodoheptane, 1,7-bromoiodoheptane, 1,8-bromochlorooctane, 1,8-chlorofluorooctane, 1,8-chloroiodooctane, 1,8-bromofluorooctane, 1,8-fluoroiodooctane or 1,8-bromoiodooctane, and one or a mixture of at least two thereof may be used.

Meanwhile, the compound of Formula 5 which reacts with the compound of Formula 4 is a raw material providing a tertiary amino group structure in a finally prepared aminosilane-based compound of Formula 1.

Particularly, the compound of Formula 5 may be a compound of Formula 5 where $Z^1$ and $Z^2$ are each independently a monovalent hydrocarbon group of 1 to 20 carbon atoms, which is unsubstituted or substituted with an organic group containing Si, O or N and does not include active hydrogen, or a functional group of Formula 3 below, in which at least one of the two is the functional group of Formula 3 below, and more particularly, $Z^1$ and $Z^2$ are each independently a compound having a functional group of Formula 3 below.

[Formula 3]

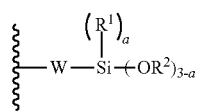

In Formula 3,
"a" may be an integer of 0 to 2, more particularly, an integer of 0 or 1,
$R^1$ and $R^2$ may be each independently an alkyl group of 1 to 10 carbon atoms, more particularly, an alkyl group of 1 to 6 carbon atoms, or a cyclic alkyl group of 3 to 6 carbon atoms, that is, a cycloalkyl group, more particularly, an alkyl group of 1 to 4 carbon atoms such as a methyl group, an ethyl group, a propyl group, an isopropyl group, a butyl group, and a t-butyl group, and
W may be an alkylene group of 1 to 10 carbon atoms, which is unsubstituted or substituted with an alkyl group of 1 to 4 carbon atoms, more particularly, an alkylene group of 1 to 6 carbon atoms, further more particularly, a linear alkylene group of 2 to 6 carbon atoms.

More particularly, the compound of Formula 5 may be a compound of Formula 5 where $Z^1$ and $Z^2$ are each independently the functional group of Formula 3, and in Formula 3, "a" is 0, W is a linear alkylene group of 3 to 6 carbon atoms, and $R^2$ is an alkyl group of 1 to 4 carbon atoms.

Further more particularly, the compound of Formula 5 may be bis((ethoxy(methyl)(phenyl)silyl)methyl)amine, bis((diethoxy(methyl)silyl)methyl)amine, 3-(diethoxy(methoxy)silyl)-N-(3-(diethoxy(methoxy)silyl)propyl)-2-methylpropane-1-amine, 3-(ethoxydimethoxysilyl)-N-(3-(ethoxydimethoxysilyl)propyl)-2-methylpropane-1-amine, 2-methyl-3-(triethoxysilyl)-N-(3-(triethoxysilyl)propyl)propane-1-amine, 5-(triethoxysilyl)-N-(3-(triethoxysilyl)propyl)pentane-1-amine, bis(2-(trimethoxysilyl)ethyl)amine, bis(2-(triethoxysilyl)ethyl)amine, bis((triethoxysilyl)methyl)amine, bis(ethoxydimethylsilyl)methyl)amine, bis((dimethoxy(methyl)silyl)methyl)amine, bis((trimethoxysilyl)methyl)amine, bis(3-(diethoxy(methoxy)silyl)propyl)amine, 2-methyl-3-(trimethoxysilyl)-N-(3-(trimethoxysilyl)propyl)propane-1-amine, bis(2-methyl-3-(trimethoxysilyl)propyl)amine, bis(8-triethoxysilyl)octyl)amine, bis(2-methyl-3-(tripropoxysilyl)propyl)amine, bis(2-methyl-3-(triethoxysilyl)propyl)amine, bis(3-(methoxydimethylsilyl)propyl)amine, bis(3-(diethoxy(methyl)silyl)-2-methylpropyl)amine, bis(2-(triisopropoxysilyl)ethyl)amine, bis(3-(ethoxydimethoxysilyl)-2-methylpropyl)amine, 8-(trimethoxysilyl)-N-(3-(trimethoxysilyl)propyl)octane-1-amine, bis(3-(triisopropylsilyl)propyl)amine, bis(8-(trimethoxysilyl)octyl)amine, bis(3-(triethoxysilyl)propyl)amine, bis(4-(triethoxysilyl)butyl)amine, bis(3-(diethoxy(methyl)silyl)propyl)amine, bis(2-(tripropoxysilyl)ethyl)amine, bis(3-(ethoxydimethoxysilyl)propyl)amine, bis(4-(trimethoxysilyl)butyl)amine, bis(3-(trimethoxysilyl)propyl)amine, bis(3-(tripropoxysilyl)propyl)amine, bis(3-(diethoxy(methoxy)silyl)-2-methylpropyl)amine, bis(3-(dimethoxy(methyl)silyl)-2-methylpropyl)amine, or bis(3-(dimethoxy(methyl)silyl)propyl)amine, and one or a mixture of at least two thereof may be used.

The amounts used of the compound of Formula 4 and the compound of Formula 5 may be appropriately determined in consideration of a stoichiometric reaction ratio, and particularly, in consideration of reaction efficiency, etc., the compound of Formula 5 may be used in a molar ratio of 0.3 to 5 based on 1 mol of the compound of Formula 4. If the molar ratio of the compound of Formula 5 is less than 0.3, unreacted compound of Formula 4 may remain after finishing the reaction, and if the molar ratio is greater than 5, it is apprehended that reaction efficiency may be deteriorated due to the use of an excessive amount of the compound of Formula 5. More particularly, the compound of Formula 5 may be used in a molar ratio of 0.6 to 1.0 based on 1 mol of the compound of Formula 4.

In addition, the reaction of the compound of Formula and the compound of Formula 5 may be performed in the presence of a base.

Particularly, the base may be an inorganic base, or an organic base. The inorganic base may include hydrides containing an alkali metal or an alkaline earth metal, such as calcium hydride, sodium hydride, and magnesium hydride; hydroxides containing an alkali metal or an alkaline earth metal, such as sodium hydroxide, potassium hydroxide, and magnesium hydroxide; or carbonates containing an alkali metal or an alkaline earth metal, such as cesium carbonate, sodium carbonate and potassium carbonate, and one or a mixture of at least two thereof may be used. In addition, the organic base may include amine-based bases such as triethylamine, trimethylamine, diisopropylamine, diisopropylethylamine, pyridine, rutidine, tetramethylethylenediamine, 1,8-diazabicyclo-7-undecene (DBU), and 1,4-diazabicyclo[2,2,2]octane (DABCO); or alkoxy-based bases such as sodium methoxide, sodium ethoxide, and potassium butoxide, and one or a mixture of at least two thereof may be used.

The base may be used in a molar ratio of 0.5 to 10 based on 1 mol of the compound of Formula 4. If the molar ratio of the base is less than 0.5, the reaction of the compound of Formula 4 with the compound of Formula 5 is insufficient, and if the molar ratio of the base is greater than 10, the control of the reaction is difficult due to the rapid increase of the reaction rate, and it is apprehended that by-products may be generated due to the excessive amount of the base. More particularly, the base may be used in a molar ratio of 0.8 to 1.0 based on 1 mol of the compound of Formula 4.

In addition, the reaction of the compound of Formula 4 and the compound of Formula 5 may be performed in an organic solvent, particularly, amide-based solvents such as N,N-dimethylformamide (DMF) and dimethyl acetamide (DMA); ether-based solvents such as tetrahydrofuran (THF); ketone-based solvents such as methyl ethyl ketone (MEK) and methyl isobutyl ketone (MIBK); sulfoxide-based solvents such as dimethyl sulfoxide; nitrile-based solvents such as acetonitrile; or alcohol-based solvents such as isopropyl alcohol (IPA), and one or a mixture of at least two thereof may be used. More particularly, amide-based solvents may be used.

More particularly, the reaction of the compound of Formula 4 and the compound of Formula 5 may be performed by dissolving each of the compound of Formula 4 and the compound of Formula 5 in an organic solvent to prepare each solution phase, and then, mixing thereof. In this case, the base may be included in the solution including the compound of Formula 4.

In addition, the reaction of the compound of Formula 4 and the compound of Formula 5 may be performed at a temperature of 0° C. to 100° C., more particularly, at a temperature of 18° C. to 25° C.

By reacting the compound of Formula 4 and the compound of Formula 5 according to the above-described conditions and processes, a compound of Formula 2 below, in which a halogen group ($X^2$) which has smaller electronegativity among two halogen groups in the compound of Formula 4 is substituted with a secondary amino group in the compound of Formula 5, is produced.

[Formula 2]

In Formula 2, $X^1$, Y, $Z^1$ and $Z^2$ are the same as defined above.

Then, step 2 in the preparation method of the aminosilane-based compound according to an embodiment of the present invention is a step for preparing the aminosilane-based compound of Formula 1 by reacting the compound of Formula 2 which is prepared in step 1 and a hetero compound.

In step 2, the hetero compound increases the interaction with a conjugated diene-based polymer by providing a hetero group containing at least one nitrogen atom to the aminosilane-based compound of Formula 1.

The hetero compound containing at least one nitrogen atom may be a linear or branched hetero compound containing at least one, more particularly, 1 to 3 nitrogen atoms in a molecule; or a heterocyclic compound.

The linear or branched hetero compound may particularly include amine, diamine or triamine, more particularly, an aliphatic amine of 1 to 20 carbon atoms.

In addition, the heterocyclic compound is a five-member or six-member ring compound containing 1 to 3 nitrogen atoms in a molecule and may be heterocycloalkane, heterocycloalkene, or heteroaryl, more particularly, imidazole, piperazine, methylpiperazine, pyridine, or pyrrole, and one or a mixture of at least two thereof may be used.

In addition, at least one hydrogen atom in the hetero compound may be substituted with an alkyl group of 1 to 8 carbon atoms, an alkoxy group of 1 to 8 carbon atoms, an aryl group of 6 to 12 carbon atoms, a halogen group, a carboxyl group, an aldehyde group, an acyl group, or a cyano group.

The hetero compound may be used in a stoichiometric ratio relative to the compound of Formula 2, particularly, in a molar ratio of 0.5 to 5 based on 1 mol of the compound of Formula 2. If the molar ratio of the hetero compound is less than 0.5, reaction yield is low, and if the molar ratio is greater than 5, it is apprehended that reaction efficiency may be deteriorated due to the use of an excessive amount of the hetero compound. More particularly, the hetero compound may be used in a molar ratio of 1.0 to 1.2 based on 1 mol of the compound of Formula 4.

In addition, the reaction of the compound of Formula 2 and the hetero compound may be performed in the presence of of a base such as an amine.

The base plays the role of promoting the reaction of the compound of Formula 2 and the hetero compound, and particularly, the base may be an inorganic base, or an organic base. The inorganic base may include hydrides containing an alkali metal or an alkaline earth metal, such as calcium hydride, sodium hydride and magnesium hydride; hydroxides containing an alkali metal or an alkaline earth metal, such as sodium hydroxide, potassium hydroxide and magnesium hydroxide; or carbonates containing an alkali metal or an alkaline earth metal, such as cesium carbonate, sodium carbonate and potassium carbonate, and one or a mixture of at least two thereof may be used. In addition, the organic base may include amine-based bases such as triethylamine, trimethylamine, diisopropylamine, diisopropylethylamine, pyridine, rutidine, tetramethylethylenediamine, 1,8-diazabicyclo-7-undecene (DBU) and 1,4-diazabicyclo[2,2,2]octane (DABCO); or alkoxy-based bases such as sodium methoxide, sodium ethoxide and potassium butoxide, and one or a mixture of at least two thereof may be used. More particularly, a tertiary amine containing an alkyl group of 1 to 10 carbon atoms such as triethylamine and trimethylamine may be used, and one or a mixture of at least two thereof may be used.

The base may be used in a molar ratio of 0.5 to 5.0 based on 1 mol of the compound of Formula 2. If the molar ratio of the base is less than 0.5, the reaction yield may be degraded, and if the molar ratio of the base is greater than 5.0, the reaction efficiency may be degraded. More particularly, the base may be used in a molar ratio of 1.3 to 2.1 based on 1 mol of the compound of Formula 2.

In addition, the reaction of the compound of Formula and the hetero compound may be performed in an organic solvent. The organic solvent may particularly include nitrile-based solvents such as acetonitrile, amide-based solvents such as N,N-dimethylformamide (DMF) and dimethyl acetamide (DMA); ether-based solvents such as tetrahydrofuran (THF); ketone-based solvents such as methyl ethyl ketone (MEK) and methyl isobutyl ketone (MIBK); sulfoxide-based solvents such as dimethyl sulfoxide; or alcohol-based solvents such as isopropyl alcohol (IPA), and one or a mixture of at least two thereof may be used. More particularly, nitrile-based solvents may be used.

More particularly, the reaction of the compound of Formula 2 and the hetero compound may be performed by dissolving each of the compound of Formula 2 and the hetero compound in the organic solvent to prepare each solution phase, and then mixing thereof. In this case, the base may be added to the solution including the compound of Formula 2.

In addition, the reaction of the compound of Formula 2 and the hetero compound may be performed at a temperature of −20° C. to 100° C., more particularly, at a temperature of 60° C. to 70° C.

More particularly, in step 2, the hetero compound is dissolved in the organic solvent, and a base material is added thereto to prepare a mixture solution. To the resultant mixture solution, the solution prepared by dissolving the compound of Formula 2 in an organic solvent is added, and the reaction temperature is increased in the temperature range. Then, a solid thus produced is extracted with a nonpolar solvent such as hexane to prepare the aminosilane-based compound of Formula 1. In this case, the extraction process may be performed by a common method, and after the extraction process, a concentration process in a reduced pressure for removing an extraction solvent may be selectively further performed according to a common method.

If the compound of Formula 2 and the hetero compound are reacted according to the above conditions and processes, the aminosilane-based compound of Formula 1, in which a halogen group ($X^1$) is substituted with a hetero group (A) derived from the hetero compound in the compound of Formula 2 is prepared.

More particularly, the preparation method of an aminosilane-based compound of Formula 1 according to an embodiment of the present invention includes a step of reacting a compound of Formula 2 below with a hetero compound containing at least one nitrogen atom, and selectively further includes a step of preparing the compound of Formula 2 by reacting a compound of Formula 4 below and a compound of Formula 5 below in the presence of a base, prior to the reaction of the compound of Formula 2 and the hetero compound.

[Formula 1]

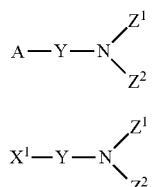

[Formula 2]

$$X^1-Y-N\begin{matrix}Z^1\\Z^2\end{matrix}$$

In Formula 1 and Formula 2,

A is a functional group derived from the hetero compound containing at least one nitrogen atom, $X^1$ is a halogen group, Y is a divalent hydrocarbon group of 1 to 20 carbon atoms, more particularly, an alkylene group of 2 to 20 carbon atoms, or 2 to 10 carbon atoms, and $Z^1$ and $Z^2$ are each independently a functional group of Formula 3 below.

[Formula 3]

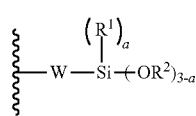

In Formula 3,

"a" is an integer of 0 to 2, $R^1$ and $R^2$ are each independently a monovalent hydrocarbon group of 1 to 10 carbon atoms, and W is a divalent hydrocarbon group of 1 to 10 carbon atoms, which is unsubstituted or substituted with an alkyl group of 1 to 4 carbon atoms.

[Formula 4]

$$X^1-Y-X^2$$

[Formula 5]

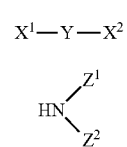

In Formula 4 and Formula 5, $X^1$ and $X^2$ are each independently a halogen group, where $X^2$ is a halogen group having a smaller electronegativity than $X^1$, Y is a divalent hydrocarbon group of 1 to 20 carbon atoms, more particularly, an alkylene group of 2 to 20 carbon atoms, and $Z^1$ and $Z^2$ may be each independently a functional group of the above Formula 3, and in this case, in Formula 3, W, $R^1$, $R^2$ and "a" are the same as defined above.

In an embodiment, the preparation method may be a method for preparing an aminosilane-based compound of Formula 1a below, including a step of reacting a compound of Formula 2a below with imidazole or 4-methylpiperazine.

[Formula 1a]

[Formula 1b]

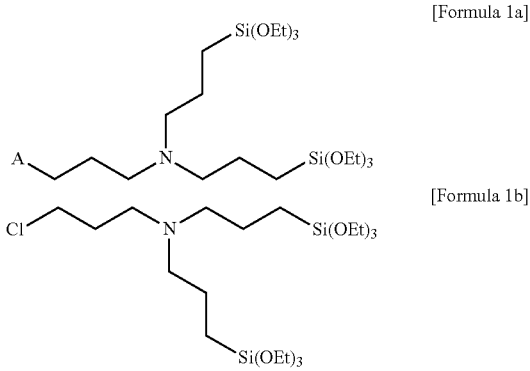

In Formula 1a and Formula 2a, A is an imidazol-1-yl group or a 4-methylpiperazine-1-yl group, and OEt is an ethoxy group.

The preparation method of an aminosilane-based compound of Formula 1 according to another embodiment of the present invention, more particularly, includes a step of reacting a compound of Formula 2 below with a hetero compound containing at least one nitrogen atom, and selectively further includes a step of preparing the compound of Formula 2 by reacting a compound of Formula 4 below and a compound of Formula 5 below in the presence of a base, prior to the reaction of the compound of Formula 2 and the hetero compound.

[Formula 1]

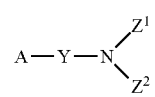

[Formula 2]

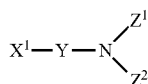

In Formula 1 and Formula 2,

A is a functional group derived from the hetero compound containing at least one nitrogen atom, $X^1$ is a halogen group, Y is a divalent hydrocarbon group of 1 to 20 carbon atoms, more particularly, an alkylene group of 1 to 10 carbon atoms, $Z^1$ is a monovalent hydrocarbon group of 1 to 20 carbon atoms, which is unsubstituted or substituted with an organic group including Si, O or N and does not contain active hydrogen, particularly, an alkyl group of 1 to 10 carbon atoms, more particularly, an alkyl group of 1 to 6 carbon atoms such as a methyl group, an ethyl group, a propyl group, and a t-butyl group, and $Z^2$ is a functional group of Formula 3 below.

[Formula 3]

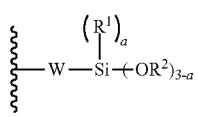

In Formula 3,

"a" is an integer of 0 to 2, $R^1$ and $R^2$ are each independently a monovalent hydrocarbon group of 1 to 10 carbon atoms, more particularly, an alkyl group of 1 to 10 carbon atoms, and W is a divalent hydrocarbon group of 1 to 10 carbon atoms, which is unsubstituted or substituted with an alkyl group of 1 to 4 carbon atoms, more particularly, an alkylene group of 1 to 10 carbon atoms, which is unsubstituted or substituted with an alkyl group of 1 to 4 carbon atoms.

[Formula 4]

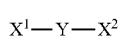

[Formula 5]

In Formula 4 and Formula 5, $X^1$ and $X^2$ are each independently a halogen group, where $X^2$ is a halogen group having a smaller electronegativity than $X^1$, Y is a divalent hydrocarbon group of 1 to 20 carbon atoms, more particularly, an alkylene group of 2 to 20 carbon atoms, $Z^1$ is a monovalent hydrocarbon group of 1 to 20 carbon atoms, which is unsubstituted or substituted with an organic group including Si, O or N and does not contain active hydrogen, particularly, an alkyl group of 1 to 20 carbon atoms, more particularly, an alkyl group of 1 to 6 carbon atoms such as a methyl group, an ethyl group, a propyl group, and a t-butyl group, and $Z^2$ is a functional group of the above Formula 3.

In an embodiment, the preparation method may be a method for preparing an aminosilane-based compound of Formula 1b below, including a step of reacting a compound of Formula 2b below and dimethylamine.

[Formula 1b]

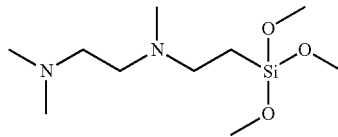

[Formula 2b]

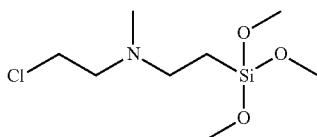

According to the preparation method, an aminosilane-based compound of Formula 1 with high purity may be prepared in high yield without concerning the remaining of unreacted aminosilane, particularly, secondary aminosilane and the removal thereof, by selectively and sequentially introducing an alkoxysilylamino group and a hetero group, by using a halogenated alkane compound containing halogen functional groups having different reactivity. In addition, the aminosilane-based compound of Formula 1 prepared by the preparation method includes a hetero group having excellent interaction with a conjugated diene-based polymer, and a conjugated diene-based polymer may be modified with excellent efficiency.

Therefore, according to another embodiment of the present invention, there is provided a modifier including the aminosilane-based compound of Formula 1 prepared by the preparation method.

Particularly, in the modifier, the aminosilane-based compound of Formula 1 imparts a conjugated diene polymer with a functional group to modify the polymer via substitution or addition reaction with an active metal part in the conjugated diene polymer having an active metal part. More particularly, the aminosilane-based compound of Formula 1 includes a tertiary amino group showing high reactivity with respect to the active part of the conjugated diene-based polymer, and may modify the conjugated diene-based polymer in a high modification ratio. As a result, a functional group derived from the aminosilane-based compound of Formula 1 may be introduced into the conjugated diene-based polymer in high yield. In addition, in the aminosilane-based compound of Formula 1, the tertiary amino group improves the affinity of a modified and conjugated diene-based polymer with a filler in a rubber composition. In detail, the tertiary amino group inhibits hydrogen bonding between hydroxide groups which are present at the surface of an inorganic filler and prevents the agglomeration between inorganic fillers, thereby improving the dispersibility of the inorganic filler in a rubber composition. As described above, the modifier has an optimized structure which may maximize the affinity with an inorganic filler and a solvent, and thus, a modified and conjugated diene-based polymer which may improve the abrasion resistance, the low consumption ratio and the processability of a rubber composition with good balance, may be prepared with high efficiency. In the present invention, the solubility of the modifier means the degree of clear dissolution without turbidity when observed with a naked eye.

More particularly, the aminosilane-based compound of Formula 1 may be one compound among Formula 1a-1, Formula 1a-2, Formula 1b and Formula 1c below.

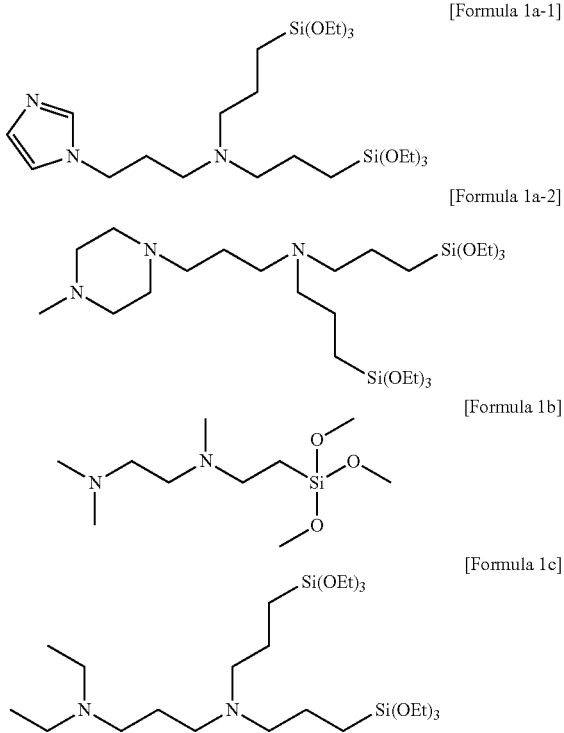

[Formula 1a-1]

[Formula 1a-2]

[Formula 1b]

[Formula 1c]

In addition, the modifier according to an embodiment of the present invention is produced during the preparation process of the aminosilane-based compound of Formula 1, and may further include at least one compound of Formula 6 and Formula 7 below, which are not separated and remaining afterward.

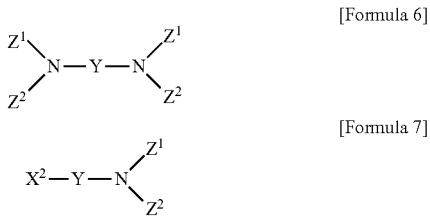

[Formula 6]

[Formula 7]

In Formula 6 and Formula 7, $X^2$, $Z^1$ and $Z^2$ are the same as defined above.

If the modifier according to an embodiment of the present invention further includes at least one compound of Formula 6 and Formula 7, the amount added thereof may be in an amount range not inhibiting the effects of the modifier, particularly, in an amount of 0.01% or less based on the total amount of the modifier.

In addition, according to another embodiment of the present invention, there is provided a modified and conjugated diene-based polymer which is modified using the modifier.

The modified and conjugated diene-based polymer is prepared by modifying a conjugated diene-based polymer using the modifier and may include a functional group derived from the aminosilane-based compound of Formula 1, and more particularly, a conjugated diene-based polymer chain may be combined with at least one tertiary amino group.

In addition, if the modifier is produced during the preparation process of the aminosilane-based compound of Formula 1 and further includes at least one compound of Formula 6 and Formula 7, which are not separated and remaining during a separation process afterward, the modified and conjugated diene-based polymer may further include a functional group derived from the compounds.

Meanwhile, the conjugated diene-based polymer may be a homopolymer of a conjugated diene-based monomer or a copolymer of a conjugated diene-based monomer and an aromatic vinyl-based monomer.

In addition, if the modified and conjugated diene-based polymer is a copolymer, the copolymer may be a random copolymer in which structure units composing the copolymer in addition to the structure unit derived from the conjugated diene-based monomer and the structure unit derived from the aromatic vinyl-based monomer are arranged in disorder.

Particularly, the modified and conjugated diene-based polymer may have a narrow molecular weight distribution (Mw/Mn) of 1.1 to 3.0. If the molecular weight distribution of the modified and conjugated diene-based polymer is greater than 3.0 or less than 1.1, and applied in a rubber composition, it is apprehended that elasticity properties and viscoelasticity may be deteriorated. In consideration of the remarkable improvement of the elasticity properties and viscoelasticity of a polymer according to the control of molecular weight distribution, the molecular weight distribution of the conjugated diene-based polymer may particularly be from 1.3 to 3.0.

In the present invention, the molecular weight distribution of a modified butadiene-based polymer may be calculated from a ratio (Mw/Mn) of a weight average molecular weight (Mw) and a number average molecular weight (Mn). In this case, the number average molecular weight (Mn) is a common average of the molecular weights of individual polymers, which is obtained by measuring the molecular weight of n number of polymer molecules and calculating by dividing the total of the molecular weight by n. The weight average molecular weight (Mw) shows the molecular weight distribution of a polymer composition. The average of all molecular weights may be expressed by gram per mol (g/mol).

In addition, in the present invention, the weight average molecular weight and the number average molecular weight are molecular weights analyzed by gel permeation chromatography (GPC) with a polystyrene standard, respectively.

In addition, the modified and conjugated diene-based polymer may satisfy the molecular weight distribution conditions and at the same time, may have the number average molecular weight (Mn) of 50,000 g/mol to 2,000,000 g/mol, more particularly, 200,000 g/mol to 800,000 g/mol. In addition, the modified and conjugated diene-based polymer may have the weight average molecular weight (Mw) of 100,000 g/mol to 4,000,000 g/mol, more particularly, from 300,000 g/mol to 1,500,000 g/mol.

If the weight average molecular weight (Mw) of the modified and conjugated diene-based polymer is less than 100,000 g/mol or the number average molecular weight (Mn) is less than 50,000 g/mol, if applied to a rubber composition, tensile properties may be deteriorated. In addition, if the weight average molecular weight (Mw) is greater than 4,000,000 g/mol or the number average molecular weight (Mn) is greater than 2,000,000 g/mol, the processability of the modified and conjugated diene-based polymer is deteriorated, the workability of a rubber composition is degraded, mixing and kneading becomes difficult, and the physical properties of a rubber composition may not be sufficiently improved.

More particularly, if the modified and conjugated diene-based polymer according to an embodiment of the present invention satisfies the conditions of the molecular weight distribution with the weight average molecular weight (Mw) and the number average molecular weight at the same time, and if applied to a rubber composition, tensile properties, viscoelasticity and processability of the rubber composition may be improved in good balance without leaning to one side.

In addition, the modified and conjugated diene-based polymer may have a vinyl content of 5 wt % or more, particularly, 10 wt % or more, more particularly, 10 wt % to 50 wt %. If the vinyl content is in the range, a glass transition temperature may be controlled in an appropriate range, and thus, if applied to tires, physical properties required for tires such as running resistance and braking force may be improved.

In this case, the vinyl content represents the amount of not 1,4-added but 1,2-added conjugated diene-based monomer by the percentage based on the total amount of a conjugated diene-based polymer composed of a vinyl group-containing monomer or a conjugated diene-based monomer.

In addition, the modified and conjugated diene-based polymer according to an embodiment of the present invention may have mooney viscosity (MV) of 40 to 90, particularly, 60 to 80 at 100° C. With the mooney viscosity in the above range, excellent processability may be shown.

In the present invention, the mooney viscosity may be measured by using a mooney viscometer, for example, MV2000E of Monsanto Co., Ltd. using Large Rotor at a rotor speed of 2±0.02 rpm at 100° C. In this case, a specimen used was stood at room temperature (23±3° C.) for 30 minutes or more, and 27±3 g of the specimen was collected and put in a die cavity, and then, Platen was operated.

According to another embodiment of the present invention, there is provided a method for preparing the modified and conjugated diene-based polymer using the modifier including the aminosilane-based compound of Formula 1.

The preparation method includes a step of preparing an active polymer of which at least one terminal is combined with a metal by polymerizing conjugated diene-based monomers, or an aromatic vinyl-based monomer and a conjugated diene-based monomer in the presence of an organic metal compound in a hydrocarbon solvent (step 1); and a step of reacting the active polymer with a modifier including the aminosilane-based compound of Formula 1 (step 2).

Step 1 is a step for preparing an active polymer of which at least one terminal is combined with a metal, and is performed by polymerizing conjugated diene-based monomers, or an aromatic vinyl-based monomer and a conjugated diene-based monomer in the presence of an organic metal compound in a hydrocarbon solvent.

The polymerization of step 1 may use a conjugated diene-based monomer alone, or a conjugated diene-based monomer and an aromatic vinyl-based monomer together as the monomer. That is, the polymer prepared by the preparation method according to an embodiment of the present invention may be a conjugated diene-based monomer homopolymer, or a copolymer derived from a conjugated diene-based monomer and an aromatic vinyl-based monomer.

The conjugated diene-based monomer may be, for example, at least one selected from the group consisting of 1,3-butadiene, 2,3-dimethyl-1,3-butadiene, piperylene, 3-butyl-1,3-octadiene, isoprene, and 2-phenyl-1,3-butadiene, without specific limitation.

If the conjugated diene-based polymer and the aromatic vinyl-based monomer are used together as the monomer, the conjugated diene-based monomer may be used in an amount such that an amount of the derived unit of the conjugated diene-based monomer in a finally prepared modified and conjugated diene-based polymer is 60 wt % or more, particularly, from 60 wt % to 90 wt %, more particularly, from 60 wt % to 85 wt %.

The aromatic vinyl-based monomer may be, for example, at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl) styrene, and 1-vinyl-5-hexylnaphthalene, without specific limitation.

If the conjugated diene-based monomer and the aromatic vinyl-based monomer are used together as the monomer, the aromatic vinyl-based monomer may be used in an amount such that an amount of the derived unit from the aromatic vinyl-based monomer in a finally prepared modified and conjugated diene-based polymer is 40 wt % or less, particularly, from 10 wt % to 40 wt %, more particularly, from 15 wt % to 40 wt %.

The hydrocarbon solvent is not specifically limited and may be, for example, at least one selected from the group consisting of n-pentane, n-hexane, n-heptane, isooctane, cyclohexane, toluene, benzene and xylene.

The organo metal compound may be used from 0.1 mmol to 1.0 mmol based on 100 g of the total monomers.

The organo metal compound may be an organo-alkali metal compound, for example, at least one selected from the group consisting of methyllithium, ethyllithium, propyllithium, n-butyllithium, s-butyllithium, t-butyllithium, hexyllithium, n-decyllithium, t-octyllithium, phenyllithium, 1-naphthyl lithium, n-eicosyl lithium, 4-butylphenyl lithium, 4-tolyl lithium, cyclohexyl lithium, 3,5-di-n-heptylcyclohexyl lithium, 4-cyclopentyl lithium, naphthyl sodium, naphthyl potassium, lithium alkoxide, sodium alkoxide, potassium alkoxide, lithium sulfonate, sodium sulfonate, potassium sulfonate, lithium amide, sodium amide, potassium amide, and lithium isopropylamide, without specific limitation.

The polymerization of step 1 may be conducted by further adding a polar additive as needed, and the polar additive may be added in an amount of 0.001 parts by weight to 1.0 parts by weight based on 100 parts by weight of the total monomers. Particularly, the addition amount may be from 0.005 parts by weight to 0.5 parts by weight, more particularly, from 0.01 parts by weight to 0.3 parts by weight based on 100 parts by weight of the total monomers.

The polar additive may be at least one selected from the group consisting of tetrahydrofuran, ditetrahydrofurylpropane, diethyl ether, cycloamyl ether, dipropyl ether, ethylene dimethyl ether, ethylene dimethyl ether, diethyl glycol, dimethyl ether, tertiary butoxyethoxyethane, bis(3-dimethylaminoethyl)ether, (dimethylaminoethyl) ethyl ether, trimethylamine, triethylamine, tripropylamine, and tetramethylethylenediamine.

In the preparation method according to an embodiment of the present invention, when a conjugated diene-based monomer and an aromatic vinyl-based monomer are copolymerized, the difference of the reaction rates between them may be compensated by the addition of the polar additive, and the easy formation of a random copolymer may be induced.

The polymerization of step 1 may be conducted by an adiabatic polymerization, or a polymerization at a constant temperature.

Here, the adiabatic polymerization means a polymerization method including a step of polymerization using self-generated heat of reaction without optionally applying heat after adding an organo-alkali metal compound. The polymerization at a constant temperature means a polymerization method by which the temperature of a polymer is kept constant by optionally applying heat or taking heat after adding the organo-alkali metal compound.

The polymerization may be conducted in a temperature range of −20° C. to 200° C., particularly, 0° C. to 150° C., more particularly, 10° C. to 120° C.

Step 2 is a step of reacting the active polymer and the modifier including the aminosilane-based compound of Formula 1 to prepare a modified and conjugated diene-based polymer.

In this case, the aminosilane-based compound of Formula 1 and the modifier including the same may be the same as described above. The modifier including the aminosilane-based compound of Formula 1 may be used in a ratio of 0.1 mol to 2.0 mol based on 1 mol of an organo-alkali metal compound.

The reaction of step 2 is modification reaction for introducing a functional group into a polymer, and the reaction may be conducted in a temperature range of 0° C. to 90° C. for 1 minute to 5 hours.

The preparation method according to an embodiment of the present invention may further include at least one step of recovering and drying of solvents and unreacted monomers after step 2, if needed.

A modified and conjugated diene polymer including a functional group having affinity with an inorganic filler and a functional group having affinity with a solvent in a polymer, and having a high modification ratio is prepared by the preparation method of a modified and conjugated diene-based polymer according to an embodiment of the present invention as described above. The modified and conjugated diene polymer includes a functional group having affinity with an inorganic filler in a molecule, and if applied to a rubber composition, excellent affinity with the inorganic filler may be shown. As a result, if applied to a rubber composition, the physical properties of a rubber composition such as exothermic properties, tensile strength, abrasion resistance, a low consumption ratio, and wet traction, and processability may be improved.

Further, according to another embodiment of the present invention, a compound having the structure of Formula 2 below is provided as a useful novel intermediate compound for preparing the aminosilane-based compound of Formula 1.

[Formula 2]

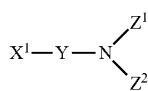

$X^1$ is a halogen group,

Y is a divalent hydrocarbon group of 1 to 20 carbon atoms, more particularly, 2 to 20 carbon atoms, and $Z^1$ and $Z^2$ are each independently a monovalent hydrocarbon group of 1 to 20 carbon atoms, which is unsubstituted or substituted with an organic group containing Si, O or N and does not contain active hydrogen, or a functional group of Formula 3 below, wherein at least one of the two is a functional group of Formula 3 below, and more particularly, $Z^1$ and $Z^2$ are each independently a functional group of Formula 3 below.

[Formula 3]

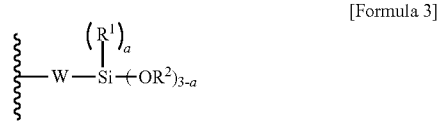

"a" is an integer of 0 to 2, $R^1$ and $R^2$ are each independently a monovalent hydrocarbon group of 1 to 10 carbon atoms, and W is a divalent hydrocarbon group of 1 to 10 carbon atoms, which is unsubstituted or substituted with an alkyl group of 1 to 4 carbon atoms.

More particularly, the compound of Formula 2 may be a compound of Formula 2a below.

[Formula 2a]

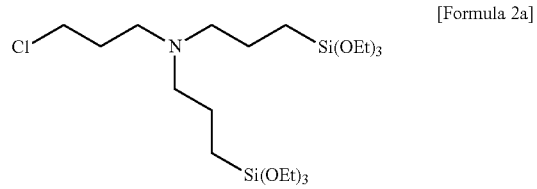

Hereinafter, the present invention will be explained in particular with reference to the following examples. However, the following examples are illustrated to assist the understanding of the present invention, and the scope of the present invention is not limited thereto.

Example 1

Step 1: Preparation of 3-chloro-N,N-bis(3-(triethoxysilyl)propyl)propane-1-amine

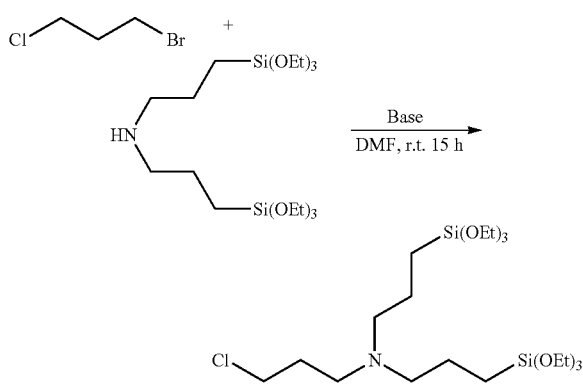

While stirring 59.0 g (375 mmol) of 1,3-bromochloropropane and 12.6 g (300 mmol) of calcium hydride in 80 ml of dimethyl formamide, 106.4 g (250 mmol) of bis(3-(triethoxysilyl)propyl)amine was dissolved in 20 ml of dimethyl formamide and slowly added thereto. The reaction solution was stirred for about 15 hours at room temperature (23° C.±3° C.). Then, solvents were removed in a reduced pressure, residues were extracted with hexane, and solvents were removed again in a reduced pressure to obtain the titled bright brown compound in an oil phase (250 mmol, >99% yield).

$^{1}$H-NMR (CDCl$_{3}$, 500 MHz) δ 3.82 (q, 12H), 3.59 (t, 2H), 2.54 (m, 2H), 2.39 (m, 4H), 1.87 (m, 2H), 1.53 (m, 4H), 1.23 (t, 18H), 0.58 (t, 4H)

Step 2: Preparation of N-(3-(1H-imidazole-1-yl)propyl)-3-(triethoxysilyl)-N-(3-(triethoxysilyl)propyl)propane-1-amine

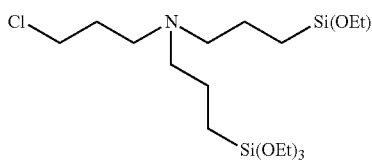

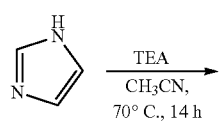

8.2 g (120 mmol) of imidazole was completely dissolved in 30 ml of acetonitrile at room temperature (23° C.±3° C.) by stirring, and 20.2 g (200 mmol) of triethylamine was added thereto. 51.2 g (100 mmol) of 3-chloro-N,N-bis(3-(triethoxysilyl)propyl)propane-1-amine was dissolved in 20 ml of acetonitrile and was added to the above reaction solution. The temperature of the resultant mixture solution was elevated to 70° C. and the reaction was conducted for about 14 hours while refluxing. After finishing the reaction, the solid thus produced was filtered, and the solvents of a filtrate were removed. The reaction product of a solid phase thus obtained was extracted with hexane, and solvents were removed under a reduced pressure to obtain 40.0 g (75 mmol, yield 75%, purity 95%) of the titled compound in a bright yellow oil phase.

$^{1}$H-NMR (DMSO, 500 MHz) δ 7.56 (s, 1H), 7.13 (s, 1H), 6.68 (s, 1H), 3.95 (t, 2H), 3.73 (q, 12H), 2.30 (m, 6H), 1.80 (t, 2H), 1.39 (m, 4H), 1.14 (t, 18H), 0.52 (t, 4H)

Example 2

Step 1: Preparation of 3-chloro-N,N-bis(3-(triethoxysilyl)propyl)propane-1-amine The titled compound was prepared by performing the same method as step 1 of Example 1.

Step 2: Preparation of 3-(4-methylpiperazine-1-yl)-N,N-bis(3-(triethoxysilyl)propyl)propane-1-amine

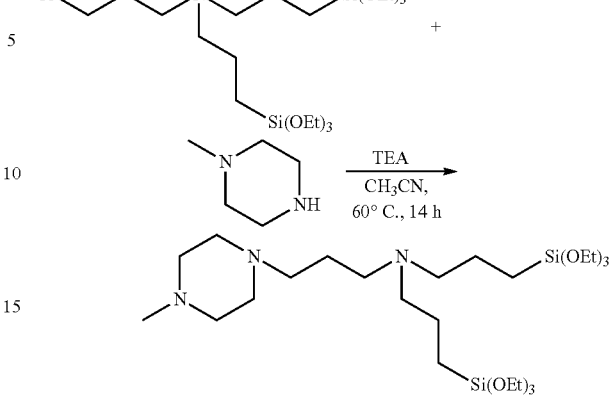

2.24 g (52.3 mmol) of 4-methylpiperazine was dissolved in 25 ml of acetonitrile, and 7.22 g (71.32 mmol) of triethylamine was added thereto. 23.88 g (47.55 mmol) of 3-chloro-N,N-bis(3-(triethoxysilyl)propyl)propane-1-amine was added at 60° C. and stirred to conduct the reaction. After finishing the reaction, the reaction product was extracted with hexane (200 ml) and concentrated under a reduced pressure to obtain the titled compound (80%) in a yellow oil phase.

$^{1}$H-NMR (CDCl$_{3}$, 500 MHz) δ 3.82 (q, 12H), 2.42 (bs, 12H), 2.35 (t, 2H), 2.29 (s, 3H), 1.63 (m, 2H), 1.53 (m, 4H), 1.22 (t, 18H), 0.57 (t, 4H)

Example 3

N-(3-(1H-imidazole-1-yl)propyl)-3-(triethoxysilyl)-N-(3-(triethoxysilyl)propyl)propane-1-amine was prepared by performing the same method in Example 1 except for using 50.6 g (500 mmol) of triethylamine instead of calcium hydride in step 1 of Example 1.

Example 4

N,N-diethyl-N,N-bis(3-(triethoxysilyl)propyl)propane-1,3-amine was prepared by performing the same method in Example 1 except for using diethylamine instead of imidazole in step 2 of Example 1.

$^{1}$H-NMR (CDCl$_{3}$, 500 MHz) δ 3.81 (q, 12H), 2.82 (m, 6H), 2.60 (t, 2H), 2.52 (dd, 4H), 1.87 (m, 2H), 1.59 (m, 4H), 1.22 (t, 24H), 0.58 (t, 4H)

Example 5

Step 1: Preparation of 2-chloro-N-methyl-N-(2-(trimethoxysilyl)ethyl)ethane-1-amine

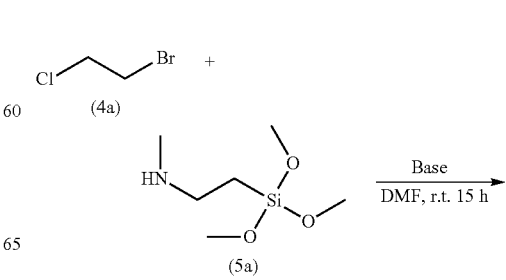

-continued

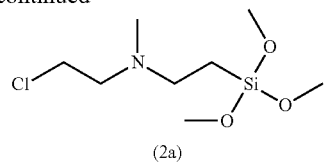

(2a)

While stirring 53.8 g (375 mmol) of 1,3-bromochloroethane and 12.6 g (300 mmol) of calcium hydride in 80 ml of dimethyl formamide, 44.8 g (250 mmol) of N-methyl-2-(trimethoxysilyl)ethane-1-amine was dissolved in 20 ml of dimethyl formamide and was slowly added thereto. The reaction solution was stirred for about 15 hours at room temperature (23° C.±3° C.). Then, solvents were removed in a reduced pressure, residues were extracted with hexane, and solvents were removed again in a reduced pressure to obtain the titled compound.

$^1$H-NMR (CDCl$_3$, 500 MHz) δ 3.82 (q, 12H), 3.59 (t, 2H), 2.54 (m, 2H), 2.39 (m, 4H), 1.87 (m, 2H), 1.53 (m, 4H), 1.23 (t, 18H), 0.58 (t, 4H)

Step 2: Preparation of N,N,N'-trimethyl-N'-(2-trimethoxysilyl)ethyl)ethane-1,2-diamine

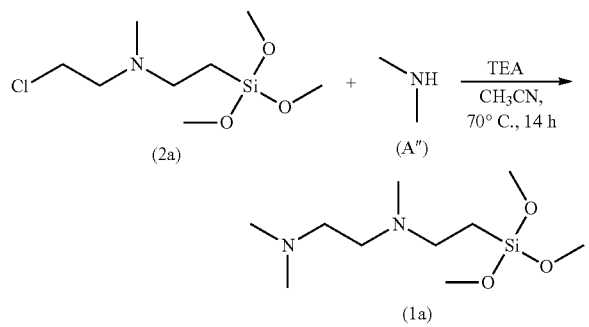

8.2 g (120 mmol) of dimethylamine was completely dissolved in 30 ml of acetonitrile at room temperature (23° C.±3° C.) by stirring, and 20.2 g (200 mmol) of triethylamine was added thereto. 24.2 g (100 mmol) of 2-chloro-N-methyl-N-(2-(trimethoxysilyl)ethyl)ethane-1-amine was dissolved in 20 ml of acetonitrile and was added to the above reaction solution. The temperature of the resultant mixture solution was elevated to 70° C. and the reaction was conducted for about 14 hours while refluxing. After finishing the reaction, the solid thus produced was filtered, and the solvents of a filtrate were removed. The reaction product of a solid phase thus obtained was extracted with hexane, and solvents were removed under a reduced pressure to obtain the titled compound.

Preparation Example 1: Preparation of Modified and Conjugated Diene Polymer

A modified and conjugated diene polymer was prepared using the aminosilane-based compound prepared in Example 1 as a modifier.

In detail, to a 20 L, autoclave reactor, 270 g of styrene, 710 g of 1,3 butadiene, 5,000 g of n-hexane and 0.9 g of 2,2-di(2-tetrahydrofuryl)propane (DTP) a polar additive were added, and the internal temperature of the reactor was controlled to 40° C. When the internal temperature of the reactor reached 40° C., 28.68 g of n-butyllithium (2.6 wt % in hexane, activation ratio=33%) was injected into the reactor, and an adiabatic reaction with heating was performed. After about 20 minutes, 20 g of 1,3-butadiene was injected for capping the terminal of SSBR with butadiene. After 5 minutes, 1.13 g of N-(3-(1H-imidazole-1-yl)propyl)-3-(triethoxysilyl)-N-(3-(triethoxysilyl)propylpropane-1-amine which was prepared in Example 1 was injected and reacted for 15 minutes (molar ratio of [DTP]/[act. Li]=1.46, molar ratio of [modifier]/[act. Li]=0.89). After that, the polymerization reaction was quenched using ethanol, and 33 g of a solution obtained by dissolving Wingstay K™ (manufactured by Eliokem, Inc.) as an antioxidant in hexane in a concentration of 0.3 wt %, was added thereto. The polymer thus obtained was added to hot water heated by steam and stirred to remove solvents, and roll dried to remove remaining solvents and water to produce a modified styrene-butadiene copolymer. The modified styrene-butadiene copolymer thus obtained was dried, and GPC analysis was conducted. The results are listed in Table 1 below.

TABLE 1

| | | | GPC analysis result | | | | |
| --- | --- | --- | --- | --- | --- | --- | --- |
| | Modifier | [modifier]/[Li] molar ratio | Mn (×10$^4$ g/mol) | Mw (×10$^4$ g/mol) | Mp (×10$^4$ g/mol) | Bonding efficiency (%) | Molecular weight distribution (Mw/Mn) |
| Pre. Example 1 | Example 1 | 0.89 | 63 | 94 | 48 126 | 46 53 | 1.49 |

Preparation Example 2, Preparation Example 3, Preparation Example 4 and Preparation Example 5: Preparation of Modified and Conjugated Diene Polymers Modified and conjugated diene-based polymers were prepared by performing the same method in Preparation Example 1 except for using the modifiers or compositions prepared in Example 2, Example 3, Example 4 and Example 5, respectively instead of the modifier prepared in Example 1.

The invention claimed is:
1. A method for preparing an aminosilane-based compound of the following Formula 1, the method comprising:

dissolving each of a compound of the following Formula 2 and a compound containing at least one nitrogen atom in an organic solvent to prepare a solution of the compound of the following Formula 2 and a solution of the compound containing at least one nitrogen atom, mixing the solution of the compound of the following Formula 2 and the solution of the compound containing at least one nitrogen atom, and reacting the compound of the following Formula 2 with the compound containing at least one nitrogen atom, wherein the compound containing at least one nitrogen atom is an aliphatic amine having 1 to 20 carbon atoms or a five-member or six-member ring compound containing 1 to 3 nitrogen atoms, and optionally at least one hydrogen atom in the compound is independently substituted with an alkyl group of 1 to 8 carbon atoms, an alkoxy group of 1 to 8 carbon atoms, an aryl group of 6 to 12 carbon atoms, a halogen group, a carboxyl group, an aldehyde group, an acyl group or a cyano group,

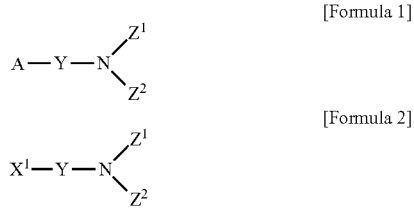

[Formula 1]

[Formula 2]

in Formula 1 and Formula 2,

A is an aliphatic amino group having 1 to 20 carbon atoms or a four-member or six-member ring containing 1 to 3 nitrogen atoms, and optionally at least one hydrogen atom in the aliphatic amino group or the five-member or six-member ring is independently substituted with an alkyl group of 1 to 8 carbon atoms, an alkoxy group of 1 to 8 carbon atoms, an aryl group of 6 to 12 carbon atoms, a halogen group, a carboxyl group, an aldehyde group, an acyl group or a cyano group, $X^1$ is a halogen group, Y is a divalent hydrocarbon group of 1 to 20 carbon atoms, and $Z^1$ and $Z^2$ are each independently a group of the following Formula 3:

[Formula 3]

in Formula 3,

"a" is an integer of 0 to 2, $R^1$ and $R^2$ are each independently a monovalent hydrocarbon group of 1 to 10 carbon atoms, and W is a divalent hydrocarbon group of 1 to 10 carbon atoms, which is unsubstituted or substituted with an alkyl group of 1 to 4 carbon atoms.

2. The method for preparing an aminosilane-based compound of claim 1, wherein the compound of Formula 2 comprises a compound in which "a" is 0, W is a linear alkylene group of 3 to 6 carbon atoms, and $R^2$ is an alkyl group of 1 to 4 carbon atoms in Formula 3.

3. The method for preparing an aminosilane-based compound of claim 1, wherein the compound of Formula 2 is a compound of the following Formula 2a:

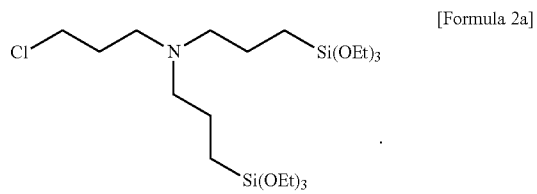

[Formula 2a]

4. The method for preparing an aminosilane-based compound of claim 1, wherein the- compound containing at least one nitrogen atom is a heterocyclic compound which comprises at least one selected from the group consisting of imidazole, piperazine, methylpiperazine, pyridine and pyrrole, wherein optionally at least one hydrogen atom in the heterocyclic compound is independently substituted with an alkyl group of 1 to 8 carbon atoms, an alkoxy group of 1 to 8 carbon atoms, an aryl group of 6 to 12 carbon atoms, a halogen group, a carboxyl group, an aldehyde group, an acyl group or a cyano group.

5. The method for preparing an aminosilane-based compound of claim 1, wherein the reaction of the compound of Formula 2 and the compound containing at least one nitrogen atom is performed in the presence of a base.

6. The method for preparing an aminosilane-based compound of claim 5, wherein the base comprises at least one selected from the group consisting of an inorganic base, an amine-based base and an alkoxy-based base.

7. The method for preparing an aminosilane-based compound of claim 1, further comprising prior to the reaction of the compound of Formula 2 and the compound containing at least one nitrogen atom, a step of preparing the compound of Formula 2 by reacting a compound of the following Formula 4 and a compound of the following Formula 5 in the presence of a base:

[Formula 4]

[Formula 5]

in Formula 4 and Formula 5, $X^1$ and $X^2$ are each independently a halogen group, where $X^2$ is a halogen group having a smaller electronegativity than $X^1$, Y is a divalent hydrocarbon group of 1 to 20 carbon atoms, and $Z^1$ and $Z^2$ are each independently the group of Formula 3.

8. The method for preparing an aminosilane-based compound of claim 7, wherein the compound of Formula 4 is selected from the group consisting of 1,2-bromochloroethane, 1,2-chlorofluoroethane, 1,2-chloroiodoethane, 1,2-bromofluoroethane, 1,2-fluoroiodoethane, 1,2-bromoiodoethane, 1,3-bromochloropropane, 1,3-chlorofluoropropane, 1,3-chloroiodopropane, 1,3-bromofluoropropane, 1,3-fluoroiodopropane, 1,3-bromoiodopropane, 1,4-bromochlorobutane, 1,4-chlorofluorobutane, 1,4-chloroiodobutane, 1,4-bromofluorobutane, 1,4-fluoroiodobutane, 1,4-bromoiodobutane, 1,5-bromochloropentane, 1,5- chlorofluoropentane, 1,5-chloroiodopentane, 1,5-bromofluoropentane, 1,5-fluoroiodopentane, 1,5-bromoiodopentane, 1,6-bromochlorohexane, 1,6-chlorofluorohexane, 1,6-chloroiodohexane, 1,6-bromofluorohexane, 1,6-fluoroiodohexane, 1,6-bromoiodohexane, 1,7-bromochloroheptane, 1,7-chlorofluoroheptane, 1,7-chloroiodoheptane, 1,7-bromofluoroheptane, 1,7-fluoroiodoheptane, 1,7-bromoiodoheptane, 1,8-bromochlorooctane, 1,8-chlorofluorooctane, 1,8-chloroiodooctane, 1,8-bromofluorooctane, 1,8-fluoroiodooctane and 1,8-bromoiodooctane.

9. The method for preparing an aminosilane-based compound of claim 7, wherein the compound of Formula 5 comprises a compound in which $Z^1$ and $Z^2$ are each independently the group of Formula 3, and in Formula 3, "a" is 0, W is a linear alkylene group of 3 to 6 carbon atoms, and $R^2$ is an alkyl group of 1 to 4 carbon atoms.

10. The method for preparing an aminosilane-based compound of claim 7, wherein the compound of Formula 5 is selected from the group consisting of bis((ethoxy(methyl)(phenyl)silyl)methyl)amine, bis((diethoxy(methyl)silyl)methyl)amine, 3-(diethoxy(methoxy)silyl)-N-(3-(diethoxy(methoxy)silyl)propyl)-2-methylpropane-1-amine, 3-(ethoxydimethoxysilyl)-N-(3-(ethoxydimethoxysilyl)propyl)-2-methylpropane-1-amine, 2-methyl -3-(triethoxysilyl)-N-(3-(triethoxysilyl)propyl)propane-1-amine, 5-(triethoxysilyl)-N-(3-(triethoxysilyl)propyl)pentane-1-amine, bis(2-(trimethoxysilyl)ethyl)amine, bis(2-(triethoxysilyl)ethyl)amine, bis((triethoxysilyl)methyl)amine, bis(ethoxydimethylsilyl)methyl)amine, bis((dimethoxy(methyl)silyl)methyl)amine, bis((trimethoxysilyl)methyl)amine, bis(3-(diethoxy(methoxy)silyl)propyl)amine, 2-methyl-3-(trimethoxysilyl)-N-(3-(trimethoxysilyl)propyl)propane-1-amine, bis(2-methyl-3-(trimethoxysilyl)propyl)amine, bis(8-triethoxysilyl)octyl)amine, bis(2-methyl-3-(tripropoxysilyl)propyl)amine, bis(2-methyl-3-(triethoxysilyl)propyl)amine, bis(3-(methoxydimethylsilyl)propyl)amine, bis(3-(diethoxy(methyl)silyl)-2-methylpropyl)amine, bis(2-(triisopropoxysilyl)ethyl)amine, bis(3-(ethoxydimethoxysilyl)-2-methylpropyl)amine, 8-(trimethoxysilyl)-N-(3-(trimethoxysilyl)propyl)octane-1-amine, bis(3-(triisopropylsilyl)propyl)amine, bis(8-(trimethoxysilyl)octyl)amine, bis(3-(triethoxysilyl)propyl)amine, bis(4-(triethoxysilyl)butyl)amine, bis(3-(diethoxy(methyl)silyl)propyl)amine, bis(2-(tripropoxysilyl)ethyl)amine, bis(3-(ethoxydimethoxysilyl)propyl)amine, bis(4-(trimethoxysilyl)butyl)amine, bis(3-(trimethoxysilyl)propyl)amine, bis(3-(tripropoxysilyl)propyl)amine, bis(3-(diethoxy(methoxy)silyl) -2-methylpropyl)amine, bis(3-(dimethoxy(methyl)silyl)-2-methylpropyl)amine and bis(3-(dimethoxy(methyl)silyl)propyl)amine.

11. The method for preparing an aminosilane-based compound of claim 7, wherein the base comprises at least one selected from the group consisting of an inorganic base, an amine-based base and an alkoxy-based base.

12. A method for preparing an aminosilane-based compound of the following Formula 1, the method comprising:
dissolving each of a compound of the following Formula 2 and a compound containing at least one nitrogen atom in an organic solvent to prepare a solution of the compound of the following Formula 2 and a solution of the compound containing at least one nitrogen atom,
mixing the solution of the compound of the following Formula 2 and the solution of the compound containing at least one nitrogen atom, and
reacting the compound of the following Formula 2 with the compound containing at least one nitrogen atom,
wherein the compound containing at least one nitrogen atom is an aliphatic amine having 1 to 20 carbon atoms or a five-member or six-member ring compound containing 1 to 3 nitrogen atoms, and optionally at least one hydrogen atom in the compound is independently substituted with an alkyl group of 1 to 8 carbon atoms, an alkoxy group of 1 to 8 carbon atoms, an aryl group of 6 to 12 carbon atoms, a halogen group, a carboxyl group, an aldehyde group, an acyl group or a cyano group,

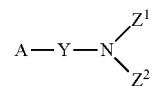

[Formula 1]

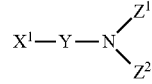

[Formula 2]

in Formula 1 and Formula 2,

A is an aliphatic amino group having 1 to 20 carbon atoms or a four-member or six-member ring containing 1 to 3 nitrogen atoms, and optionally at least one hydrogen atom in the aliphatic amino group or the five-member or six-member ring is independently substituted with an alkyl group of 1 to 8 carbon atoms, an alkoxy group of 1 to 8 carbon atoms, an aryl group of 6 to 12 carbon atoms, a halogen group, a carboxyl group, an aldehyde group, an acyl group or a cyano group, $X^1$ is a halogen group, Y is a divalent hydrocarbon group of 1 to 20 carbon atoms, and $Z^1$ and $Z^2$ are each independently a monovalent hydrocarbon group of 1 to 20 carbon atoms, which is unsubstituted or substituted with an organic group containing Si, O or N and does not contain active hydrogen, or a group of the following Formula 3, at least one of the two being the group of the following Formula 3:

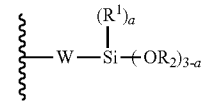

[Formula 3]

in Formula 3,

"a" is an integer of 0 to 2, $R^1$ and $R^2$ are each independently a monovalent hydrocarbon group of 1 to 10 carbon atoms, and W is a divalent hydrocarbon group of 1 to 10 carbon atoms, which is unsubstituted or substituted with an alkyl group of 1 to 4 carbon atoms.

13. The method for preparing an aminosilane-based compound of claim 12, further comprising prior to the reaction of the compound of Formula 2 and the compound containing at least one nitrogen atom, a step of preparing the compound of Formula 2 by reacting a compound of the following Formula 4 and a compound of the following Formula 5 in the presence of a base:

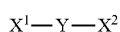
[Formula 4]

[Formula 5]

in Formula 4 and Formula 5,
$X^1$ and $X^2$ are each independently a halogen group, where $X^2$ is a halogen group having a smaller electronegativity than $X^1$,
Y is a divalent hydrocarbon group of 1 to 20 carbon atoms, and
$Z^1$ and $Z^2$ are each independently a monovalent hydrocarbon group of 1 to 20 carbon atoms, which is unsubstituted or substituted with an organic group containing Si, O or N and does not contain active hydrogen, or the group of Formula 3, at least one of the two being the group of Formula 3.

14. The method for preparing an aminosilane-based compound of claim 12, wherein the compound of Formula 2 is 2-chloro-N-methyl-N-(2-(trimethoxysilyl)ethyl)ethane-1-amine, and
the compound containing at least one nitrogen atom is dimethylamine.

15. The method for preparing an aminosilane-based compound of claim 12, wherein the compound of Formula 2 is a compound of the following Formula 2a, and
the compound containing at least one nitrogen atom is imidazole or 4-methylpiperazine:

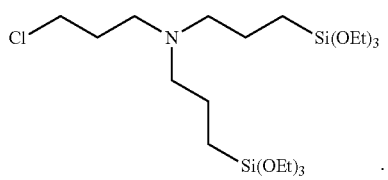
[Formula 2a]

16. A compound of the following Formula 2:

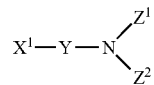
[Formula 2]

in Formula 2,
$X^1$ is a halogen group,
Y is a divalent hydrocarbon group of 1 to 20 carbon atoms, and
$Z^1$ and $Z^2$ are each independently a monovalent hydrocarbon group of 1 to 20 carbon atoms, which is unsubstituted or substituted with an organic group containing Si, O or N and does not contain active hydrogen, or a group of the following Formula 3, at least one of the two being the group of the following Formula 3:

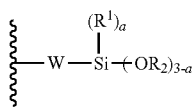
[Formula 3]

in Formula 3,
"a" is an integer of 0 to 2,
$R^1$ and $R^2$ are each independently a monovalent hydrocarbon group of 1 to 10 carbon atoms, and
W is a divalent hydrocarbon group of 1 to 10 carbon atoms, which is unsubstituted or substituted with an alkyl group of 1 to 4 carbon atoms.

\* \* \* \* \*